(12) United States Patent
Carson

(10) Patent No.: US 7,874,217 B2
(45) Date of Patent: Jan. 25, 2011

(54) METHOD AND APPARATUS FOR APPLYING AXIAL STRESS FOR WELD TESTING

(75) Inventor: Glenn Carson, Point Edward (CA)

(73) Assignee: CAR-BER Investments Inc., Point Edward (CA)

( * ) Notice: Subject to any disclaimer, the term of this patent is extended or adjusted under 35 U.S.C. 154(b) by 0 days.

(21) Appl. No.: 11/771,158

(22) Filed: Jun. 29, 2007

(65) Prior Publication Data

US 2008/0121044 A1    May 29, 2008

Related U.S. Application Data

(63) Continuation of application No. PCT/CA2005/001981, filed on Dec. 30, 2005.

(60) Provisional application No. 60/640,093, filed on Dec. 30, 2004, provisional application No. 60/663,871, filed on Mar. 22, 2005.

(51) Int. Cl.
*G01N 3/20* (2006.01)
(52) U.S. Cl. ......................................................... 73/850
(58) Field of Classification Search ................... 73/850
See application file for complete search history.

(56) References Cited

U.S. PATENT DOCUMENTS

| | | | |
|---|---|---|---|
| 1,851,345 A | 3/1932 | Brown et al. | |
| 2,242,658 A | 5/1941 | Protin | |
| 2,293,471 A | 8/1942 | Protin | |
| 2,336,524 A | 12/1943 | Bannister | |
| 2,757,536 A | 8/1956 | Heldenbrand | |
| 2,878,040 A * | 3/1959 | Hobbs | 285/288.1 |
| 2,884,986 A | 5/1959 | Heldenbrand | |
| 2,919,741 A * | 1/1960 | Strock et al. | 72/305 |
| 3,519,303 A * | 7/1970 | Gille | 294/81.6 |
| RE28,190 E * | 10/1974 | La Force et al. | 219/67 |
| 4,224,499 A | 9/1980 | Jones | |
| 4,418,860 A * | 12/1983 | LaForce | 228/196 |
| 4,516,431 A | 5/1985 | Heldenbrand | |
| 4,608,739 A * | 9/1986 | Miller | 29/421.1 |
| 4,893,944 A | 1/1990 | Leroux | |
| 5,263,362 A * | 11/1993 | Karl et al. | 73/46 |
| 5,844,127 A | 12/1998 | Berube et al. | |
| 6,029,504 A | 2/2000 | House et al. | |
| 6,032,851 A | 3/2000 | Matherne | |

(Continued)

OTHER PUBLICATIONS

Written Opinion issued in the Corresponding PCT Application No. PCT/CA2005/001981, dated Apr. 25, 2006.

(Continued)

*Primary Examiner*—Lisa M Caputo
*Assistant Examiner*—Octavia Davis
(74) *Attorney, Agent, or Firm*—Santosh K. Chari; Blake, Cassels & Graydon LLP

(57) ABSTRACT

A method for testing the integrity of a weld on a pipe includes the application of an axial stress on the weld during the integrity test. Ali assembly for performing the method is also provided, wherein a pair of circumferential supports are provided on the pipe on opposite sides of the weld, and between which extend axial force applying devices. In one aspect, the invention is used to test a weld securing a flange to a pipe. The invention also provides novel circumferential clamps for securing to the exterior of pipes.

16 Claims, 14 Drawing Sheets

U.S. PATENT DOCUMENTS

| | | | |
|---|---|---|---|
| 6,131,441 | A | 10/2000 | Berube et al. |
| 6,463,791 | B1 | 10/2002 | Berube et al. |
| 6,557,421 | B2 * | 5/2003 | Garde et al. ............... 73/850 |
| 6,581,642 | B1 * | 6/2003 | Ritchie et al. ............. 138/90 |
| 6,840,152 | B2 * | 1/2005 | Kriwet et al. ............... 92/90 |
| 6,848,322 | B2 * | 2/2005 | Scarborough ............. 73/850 |
| 6,896,171 | B2 * | 5/2005 | Den Boer et al. ........ 228/103 |
| 7,360,973 | B2 * | 4/2008 | Turner ....................... 408/92 |
| 7,669,899 | B2 * | 3/2010 | Carson ...................... 285/9.1 |

OTHER PUBLICATIONS

Supplementary European Search Report issued in the corresponding European Patent Application No. 05 85 0129, dated Feb. 18, 2010.

* cited by examiner

METHOD AND APPARATUS FOR APPLYING AXIAL STRESS FOR WELD TESTING

CROSS REFERENCE TO PRIOR APPLICATIONS

This application is a Continuation of PCT Application No. PCT/CA2005/001981, filed on Dec. 30, 2005, which claims priority from U.S. Provisional application No. 60/640,093, filed Dec. 30, 2004 and U.S. Provisional application No. 60/663,871, filed Mar. 22, 2005. The disclosures of the aforementioned related applications are incorporated herein by reference in their entirety.

BACKGROUND OF THE INVENTION

1. Field of the Invention

The present invention relates to a method and apparatus for testing welds on pipes and vessels and the like and, more particularly, for applying an axial or longitudinal stress on welds during pressure testing.

2. Description of the Prior Art

In chemical or petrochemical plants etc., it is often necessary to convey fluidic materials (e.g. liquids) from one location to another. The conveyance of such material normally includes equipment such as conduits or pipes, storage or reaction vessels etc., which are generally manufactured from metal. The joining of separate pieces of the conveying equipment is generally achieved by welding the necessary pieces together. For example, when joining adjacent ends of pipe together, it is common for each end to be provided with flanges, that are welded to each respective end, which are then bolted together to form a seal. Such flanges may also be provided on holding tanks and other such vessels so that such vessels can be connected to pipes or other vessels. Alternatively, the connections between lengths of pipe or other equipment may be welded directly together (i.e. butt welded) to form the seal. In either case, it will be appreciated that each welded joint or section must form a complete seal so as to prevent leakage of the materials being transported. This is particularly the case when handling potentially hazardous materials such as flammable or toxic liquids.

For reasons of safety, it is often necessary to periodically test the integrity of the welds used in joining the various pieces of equipment (such as pipes, vessels, flanges and the like) together.

The prior art provides various tools for conducting weld integrity tests on conduits. For example, U.S. Pat. Nos. 6,131,441 and 5,844,127 (the entire disclosures of which are incorporated herein by reference) teach weld testing tools that isolate a particular section of a pipe (such section including a weld) and subject the section to a high pressure fluid within a constrained annular space defined by the tool and the inner surface of the pipe. The pressure of the fluid within the annular space is monitored whereby any pressure drop signifies a leak in the weld.

U.S. Pat. No. 6,463,791 (the entire disclosure of which is incorporated herein by reference) teaches an apparatus for testing welds used to secure nozzles. As shown in FIG. 1 of this reference, the apparatus comprises a first seal plate that is placed on the inner surface of the vessel (for example) and a second seal plate that is secured to the outer, flange portion of the nozzle. In this manner, the nozzle volume is sealed and a pressurizing fluid is introduced therein. Once the volume is filled, the pressure is monitored as above and any leakage detected. Although this apparatus provides an accurate and efficient means of testing welds on nozzles, the size and weight of the apparatus makes it inconvenient for use on large nozzles.

Further, co-pending application Ser. No. 60/640,093 (the entire disclosure of which is incorporated herein by reference) provides a tool for testing the integrity of welds joining nozzles to vessels.

Although the above-described references provide efficient tools for testing welds, they are designed to apply essentially a radial force against the weld. In addition, there exists a need for exerting further stresses on welds for providing a "worst case scenario" so that such welds can be tested under extreme conditions.

SUMMARY OF THE INVENTION

In one aspect, the present invention generally provides a method for testing the integrity of welds on a pipe wherein an axial force is applied during the weld test process.

In another aspect, the invention generally provides an assembly for conducting an integrity test on a weld on a pipe, wherein the assembly includes at least a pair of supports on opposite sides of the weld and wherein one or more force applying devices are provided between the supports and operable there-between to generate an axial stress on the weld. One or more of the supports may comprise a clamp extending around the circumference of the pipe being tested.

In another aspect, the invention provides a circumferential clamp for mounting on pipes wherein hydraulic rams or electromagnets are used to frictionally engage the outer surface of a pipe.

Thus, in one aspect, the invention provides a method for testing the integrity of a weld on a length of pipe comprising subjecting the weld to an axial stress and conducting an integrity test on the weld.

In another aspect, the invention provides an assembly for testing the integrity of a weld on a pipe comprising:
- at least two supports anchored to the pipe and extending circumferentially around the pipe, the supports being axially spaced along the pipe and positioned on opposite sides of the weld, the supports being secured to the pipe thereby preventing axial movement of the supports along the pipe;
- at least one axial force applying device positioned between the supports, the device being adapted to apply an axial force against the supports in a direction generally parallel with a longitudinal axis of the pipe;
- a weld testing apparatus for conducting a pressure test on the weld.

In yet another aspect, the invention provides a circumferential clamp for securing to the outer diameter of a pipe comprising:
- a generally annular shaped collar having an outer diameter and an inner diameter and being adapted for placement around the circumference of the pipe;
- a plurality of hydraulic rams provided within the collar, the rams having an actuating cylinder extendable radially in a direction towards the center of the collar;
- wherein the rams are generally equidistantly spaced whereby, upon actuation of the rams, the cylinders apply a generally equal force against the outer surface of the pipe.

In yet another aspect, the invention provides a circumferential clamp for securing to the outer diameter of a pipe comprising:
- a plurality of links connected together to form a chain, the chain being sized to cover the circumference of the pipe;

each of the links including a connection means for connecting to adjacent links;

each of the links including an electromagnet, connected to a power supply, whereby upon activation of the power supply, the magnets engage the outer surface of the pipe.

BRIEF DESCRIPTION OF THE DRAWINGS

These and other features of the invention will become more apparent in the following detailed description in which reference is made to the appended drawings wherein.

DETAILED DESCRIPTION OF THE INVENTION

Throughout the description of the invention the following terms will be assumed to have the following associated meanings:

"Vessel"—will be understood to mean any equipment or apparatus to which a nozzle is attached. As such, the term "vessel" will include vessels per se, pipes, drums, and any other similar equipment. It will be understood that the term "vessel" is used herein simply as a convenient way to encompass all such equipment or apparatus.

"Annular"—this term is used to describe a body having at least one outer diameter and at least one inner diameter. Thus, an "annular tube" will be assumed to be a hollow tube with an inner and outer diameter. An "annular disc" will be assumed to be an object having an outer diameter and a central aperture thereby providing an inner diameter.

"Axial"—this term will be used to describe a direction taken along the longitudinal axis of a pipe or conduit. Thus, "axial force" or "axial stress" will be understood as being a force applied in a direction parallel to the longitudinal axis of the conduit.

Figure 1:
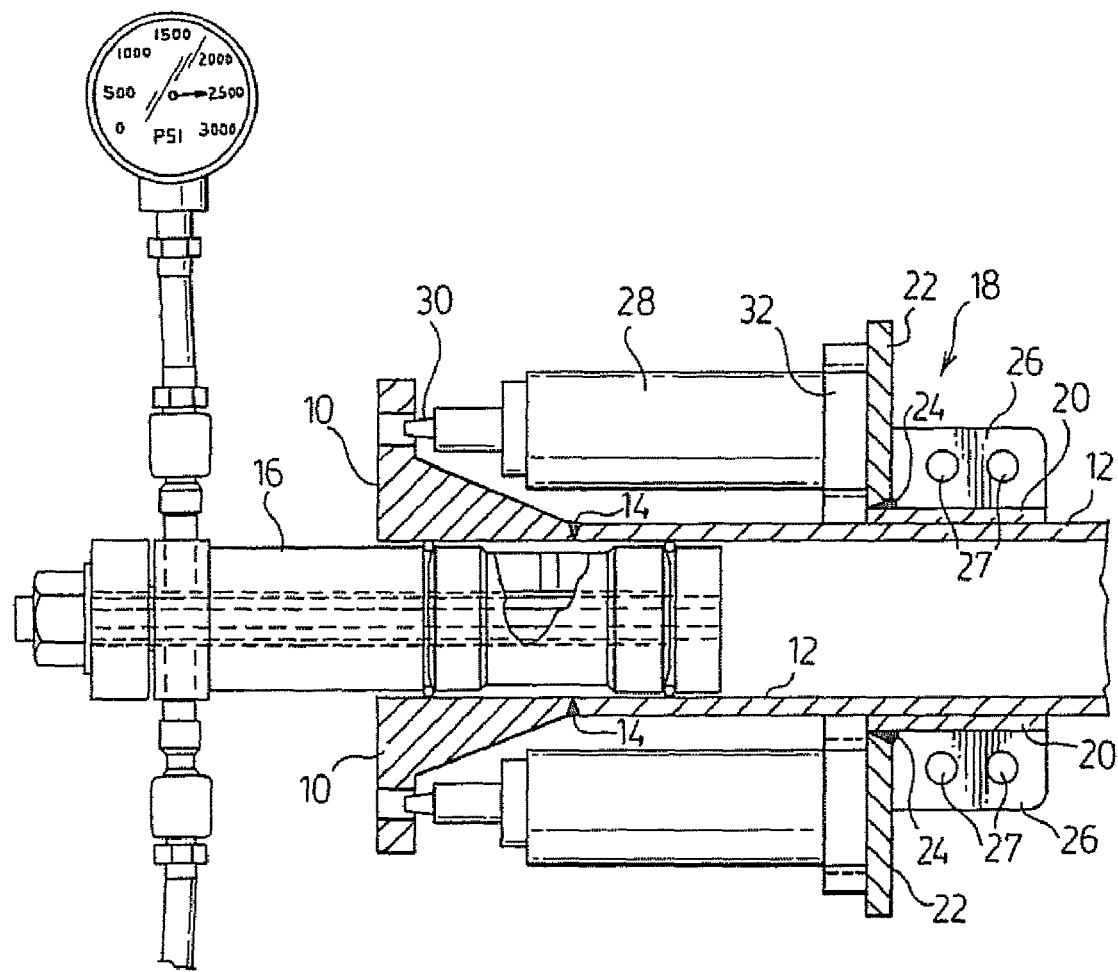
FIG. 1 is a cross sectional view of one embodiment of the present invention as used in testing welds on pipe flanges.

FIG. 1 illustrates one aspect of the invention when used in testing the welds joining a flange to an end of a pipe. As shown, the flange 10 is secured to a pipe 12 with a weld 14 as is commonly known in the art. As explained above, the weld 14 can be tested with a variety of tools known in the art. For example a testing tool 16, as described in U.S. Pat. No. 6,131,441 (incorporated herein in its entirety by reference) can be inserted within the pipe 12 and positioned proximal to the weld 14. As described in detail in U.S. Pat. No. 6,131,441, the testing tool 16 applies a radially outwardly directed pressure on the weld by forcing a pressurized fluid against the inner wall of the pipe 12. As shown, the tool applies such pressure on an isolated section of the pipe 12, in the region of the weld 14 to be tested.

As indicated above, the present invention serves to provide a further, axial stress on the weld 14 so as to subject it to extreme conditions. As will be appreciated, such added stress will result in a more dependable test result. In order to provide the axial stress, the invention provides an apparatus having a support clamp 18 that is secured to the exterior surface of the pipe 12 and spaced from the flange 10 so as to render the weld 14 to be located between the flange 10 and the support clamp 18. The clamp 18 is designed to be secured to the pipe 12 so as to provide a high frictional fit thereto. The purpose of such frictional fit is explained further below. In the aspect of the invention illustrated in FIG. 1, the clamp 18 comprises a collar portion 20 that surrounds a portion of the pipe 12 exterior. A bearing ring 22 extends perpendicularly to the collar 20 and is secured thereto by a weld 24. As an added support, the clamp may also include one or more support ribs 26, extending radially outward from, and secured to the collar 20. The ribs are secured to the collar along one edge thereof so as to extend generally parallel to the longitudinal axis of the collar 20. One end of the support ribs is positioned to abut, and thereby support, the bearing ring 22. As will be understood, the support ribs 26 serve to ensure that the bearing ring 22 maintains its position. However, it will also be understood that the ribs 26 are also provided so as to enable the support clamp 18 to be secured to the pipe being tested. That is, in one aspect, the support clamp 18 is provided in two or more sections that are placed around the outer diameter of the pipe 12. The sections of the support clamp 18 are then connected together by bolting adjacent ribs 26 together. To assist this step, the ribs 26 may be provided with cooperating holes 27 through which are passed connecting bolts. It will be understood that any means of connecting the ribs 26 may be used.

The apparatus also includes at least two and preferably a plurality of stress applying devices that are extendable in a directions parallel to the longitudinal axis of the pipe. In one aspect, such stress applying devices comprise hydraulic cylinders 28 that are circumferentially spaced around the pipe 12. The cylinders 28 are provided between the clamp 18 and the flange 10 so that a first end 30 of the cylinders 28 abuts the flange 10 while the opposite second end 32 of the cylinders abuts the bearing ring 22 of the clamp 18.

In operation, the hydraulic cylinders are actuated so as to extend in length. Such extension would, as can be seen in FIG. 1, apply an axial or longitudinal force on the flange 10 and the bearing ring 22 so as to force each away from each other. As will be understood, such force or stress would then be translated to the weld 14. It will be understood that the amount of force applied on the weld 14 may be pre-set depending on the conditions that are being tested. For example, it will be understood that the forces applied will be below the strength tolerance for the weld (or the pipe etc.). Also, it will be understood that the amount of force applied will vary from one application to another. For example, a higher force may be used in situations where the fluid being conveyed is typically under a high pressure. A lighter force may be used in situations where the fluid is under little or no stresses and the welds are not typically subject to high stresses.

It will be appreciated by persons skilled in the art that the support clamp 18 must be designed to withstand the forces applied by the hydraulic cylinders 28. As indicated above, the clamp is preferably secured to the outer surface of the pipe 12 so as to form a frictional fit. Although it is possible to weld the clamp to the outer surface of the pipe 12, it will be understood that the welding process, and, where needed, the subsequent separation of the clamp, may affect the physical integrity of the pipe 12. The clamp 18 is generally provided in at least two sections, or more if the diameter of the pipe being tested is large. In one aspect, the support clamp 18 is provided in two sections that are preferably connected together by a hinge (as explained further below). In another alternative, as indicated above, the clamp 18 can simply be provided in two or more separate sections that are bolted together through adjacent ribs, thereby avoiding the need for a hinge. The ends of the sections opposite the hinge will include a means for fastening them together. Such means for fastening may include for example bolts that can be tightened to bring the sections together. The two sections are provided over the pipe 12 and secured together as indicated above. As will be understood by persons skilled in the art, the clamp will be sized accordingly with the diameter of the pipe 12 so that tightening of the bolts or other such mechanism connecting the sections of the clamp together will result in the desired frictional fit of the clamp 18 over the pipe 12. It will further be understood by persons skilled in the art that amount of friction between the clamp 18 and the pipe 12 will depend on the force applied by the hydraulic cylinders 28. The quantification of the required frictional force can be easily calculated by methods known to persons skilled in the art. For example, once the desired amount of force to be applied on the weld is decided, the forces required by the hydraulic cylinders can then be easily calculated by dividing the weld stress by the number of cylinders. Similarly, once the required axial force to be applied by the cylinders is determined, it will be understood that it must be exceeded by the frictional force between the clamp 18 and the pipe 12. The latter will vary depending on the coefficient of friction of the clamp 18 and pipe 12 materials.

In the embodiment shown in FIG. 1, the hydraulic cylinders 28 are shown as bearing directly upon the flange 10. However, in some cases, it may be required or desired to include a spacer ring (not shown in FIG. 1) to transmit the force of the cylinders 28 to the flange 10. Such spacer rings may be necessary where, due to the position of the weld 14, the distance between the support clamp 18 and the flange 10 is longer than the cylinders 28. It will also be understood that the use of a spacer ring may also serve to evenly distribute the force of the cylinders against the flange 10. The use of spacer rings is described further in relation to FIG. 9.

Figure 2:
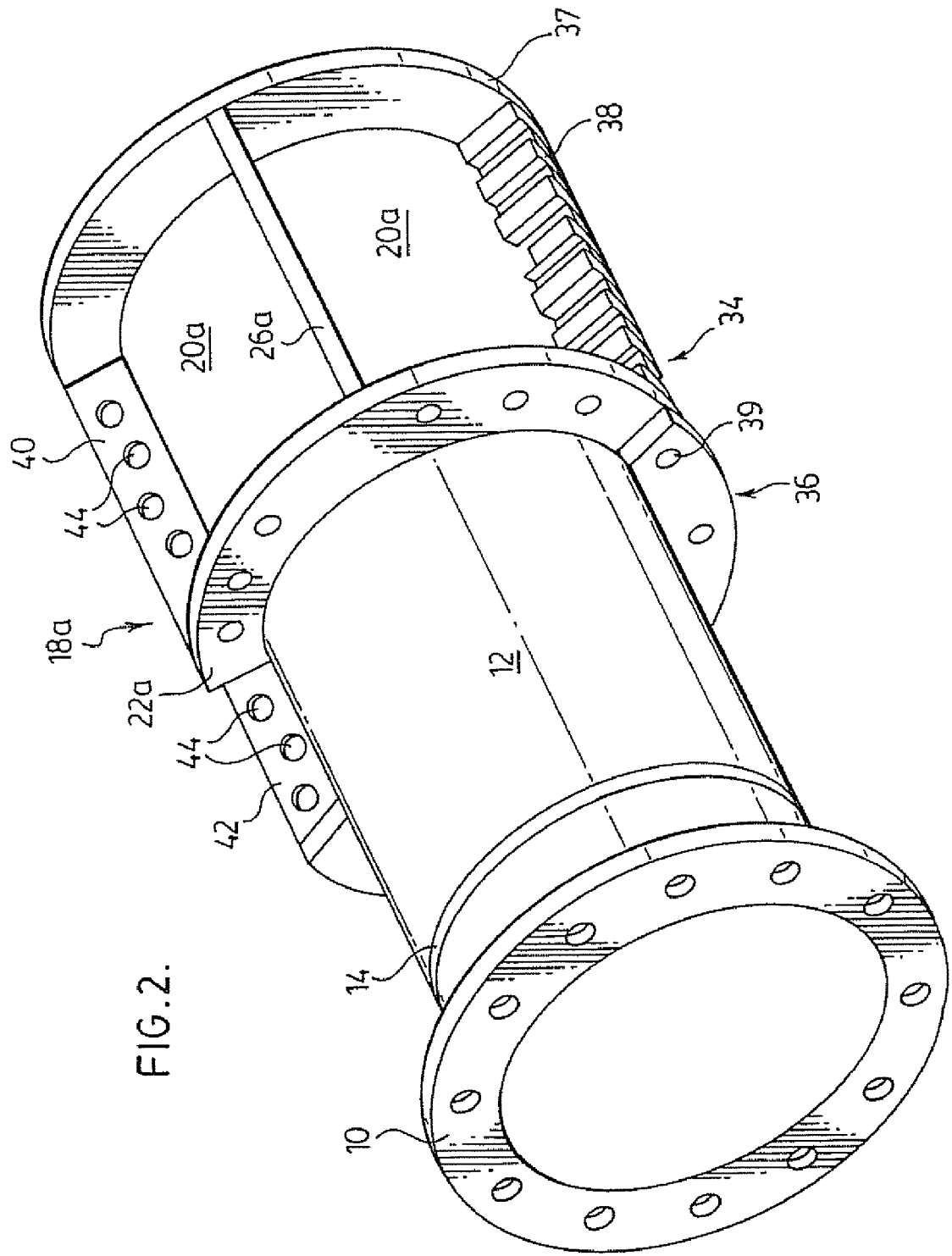
FIG. 2 is a perspective view of the apparatus of FIG. 1.

FIG. 2 illustrates an example of the clamp, identified as 18a for convenience, which is provided in two sections 34 and 36. In this aspect of the invention, the clamp includes a further support ring 37, similar to the bearing ring 22a, and positioned at the opposite end of the collar 20a. As shown, the clamp 18a includes a hinge 38 joining the two sections 34 and 36 together and which allows the clamp to be opened thereabout. The hinge 38 can comprise, for example, interlocking loops provided on each section of the clamp 18a, through which is passed a bolt 39. The two sections 34 and 36 of the clamp 18 further include a connection means, which could, for example, be longitudinally extending connection ribs or flanges 40 and 42, having bolt holes 44 for receiving bolts (not shown) as described above. As will be understood, the connection ribs 40 and 42 can also serve as the support ribs 26a described above.

Figure 3A:
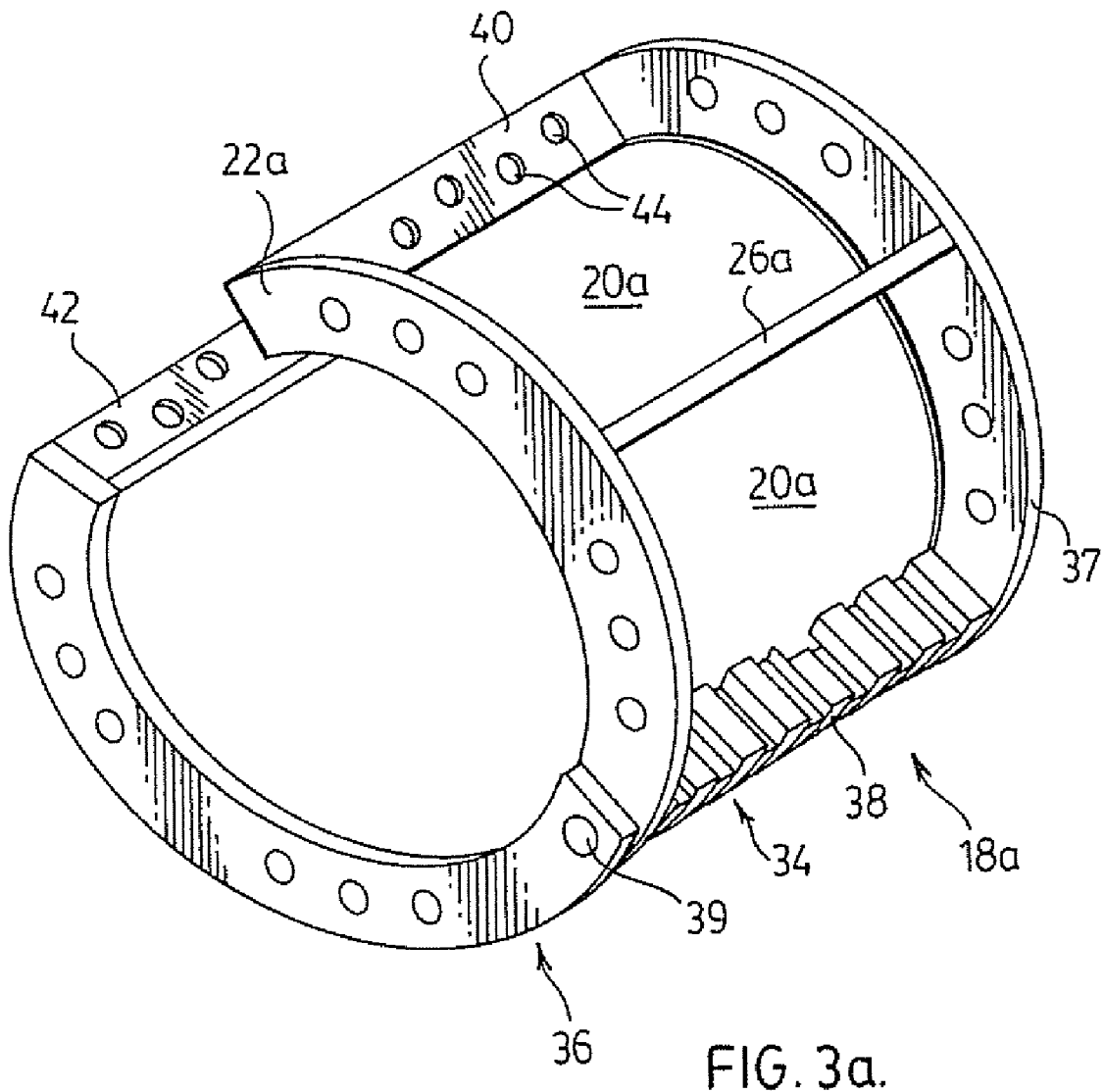
FIGS. 3a and 3e are perspective views of the support clamp of FIG. 2.
Figure 3B:
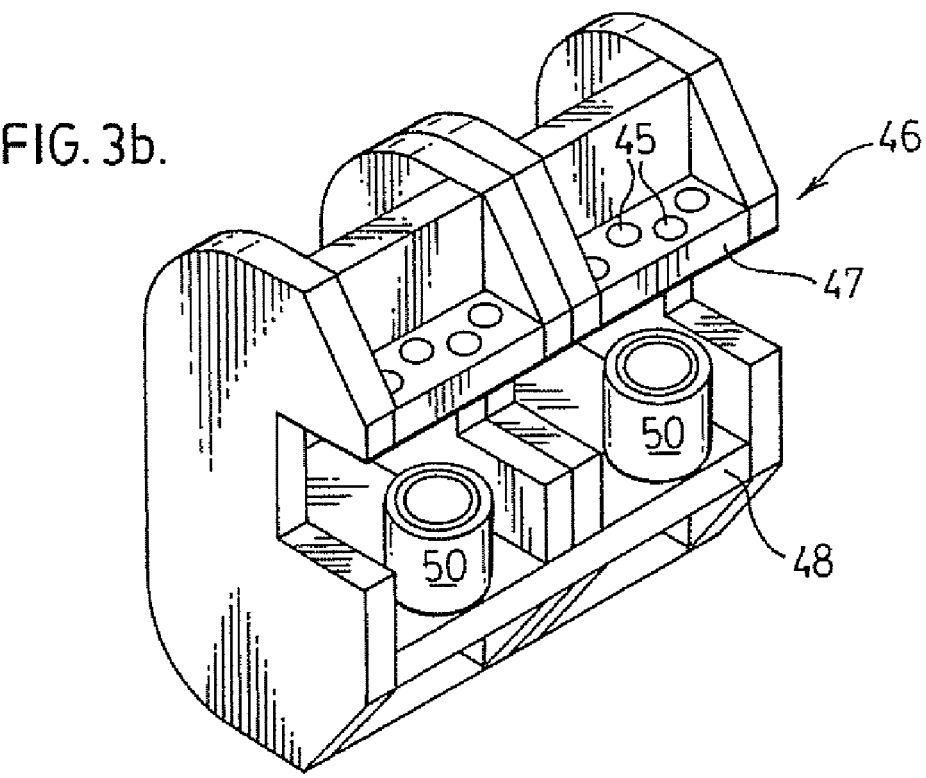
FIG. 3b is a perspective view of a hydraulic locking clamp used with the support clamp of FIG. 2.
Figure 3C:
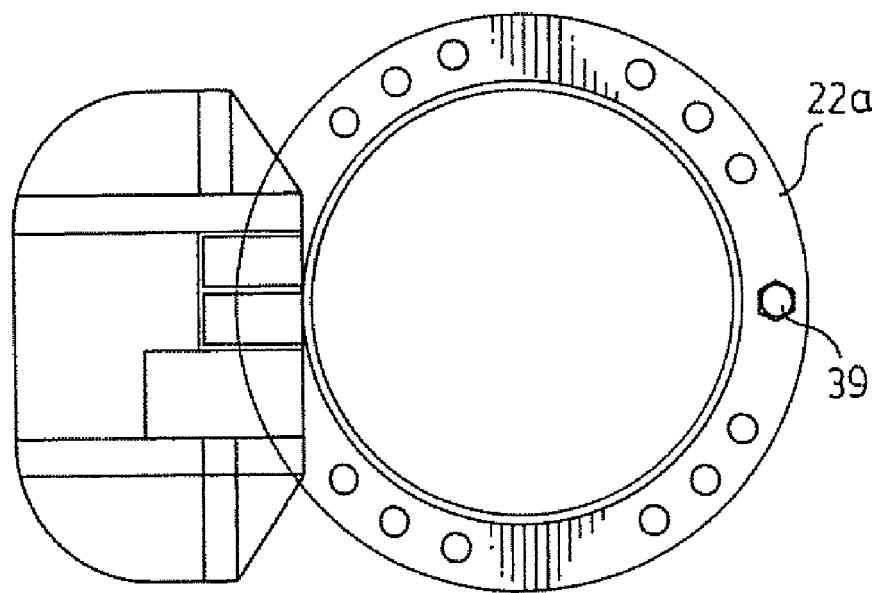
FIG. 3c is an end view of the support clamp and hydraulic locking clamp of FIGS. 3a and 3b in combination.

In another aspect, the sections 34 and 36 of the clamp 18a can be connected together by means of hydraulic clamps instead of bolts. This embodiment is illustrated in FIGS. 3a, 3b, and 3c. As shown, the sections 34 and 36 of the clamp 18a of FIG. 2 can be connected together by means of a locking clamp 46 once placed over the circumference of a pipe (not shown). The locking clamp 46 comprises a hydraulic clamp having a generally "C" shaped body including a pair of flanges 47 and 48 at the clamp's open end. A first of the flanges 47 preferably includes locating pins 49 that are adapted to be received in bolt holes 44 on one of the connection flanges 40 or 42 and serve to align the clamp 46 with same. The second of the flanges, 48, on the hydraulic clamp 46 includes at least one, and preferable two or more hydraulic cylinders 50. The flanges 47 and 48 of the hydraulic clamp 46 are designed to sandwich the connecting ribs 40 and 42 together. This is achieved by positioning the hydraulic clamp by aligning the locating pins 49 with the bolt holes 44 on one of the connecting ribs 40 or 42 wherein the first flange 47 of the hydraulic clamp is positioned on the outer side of the respective connecting rib 40 or 42. The hydraulic cylinders 50 are therefore positioned on the outer side of the other of the connecting ribs 42 or 40. As will be understood, in this arrangement, upon actuation of the cylinders 50, the ribs 40 and 42 are brought together thereby causing the clamp 18a to close and tighten about the pipe 12 (not shown).

Figure 3D:
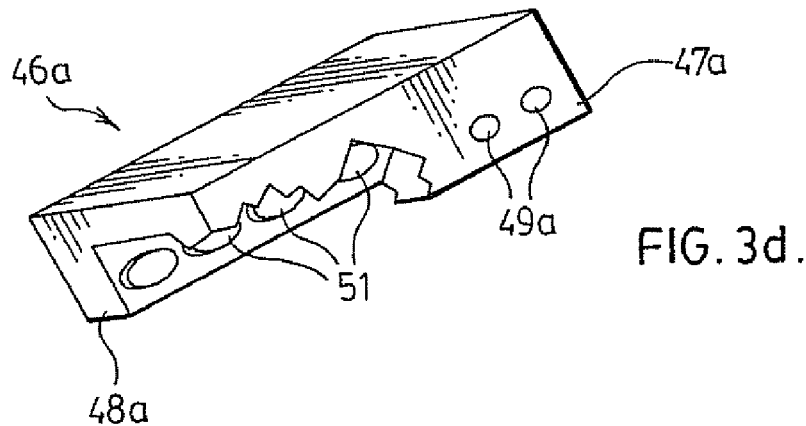
FIG. 3d is a partial perspective view of another embodiment of the locking clamp of FIG. 3b.
Figure 3E:
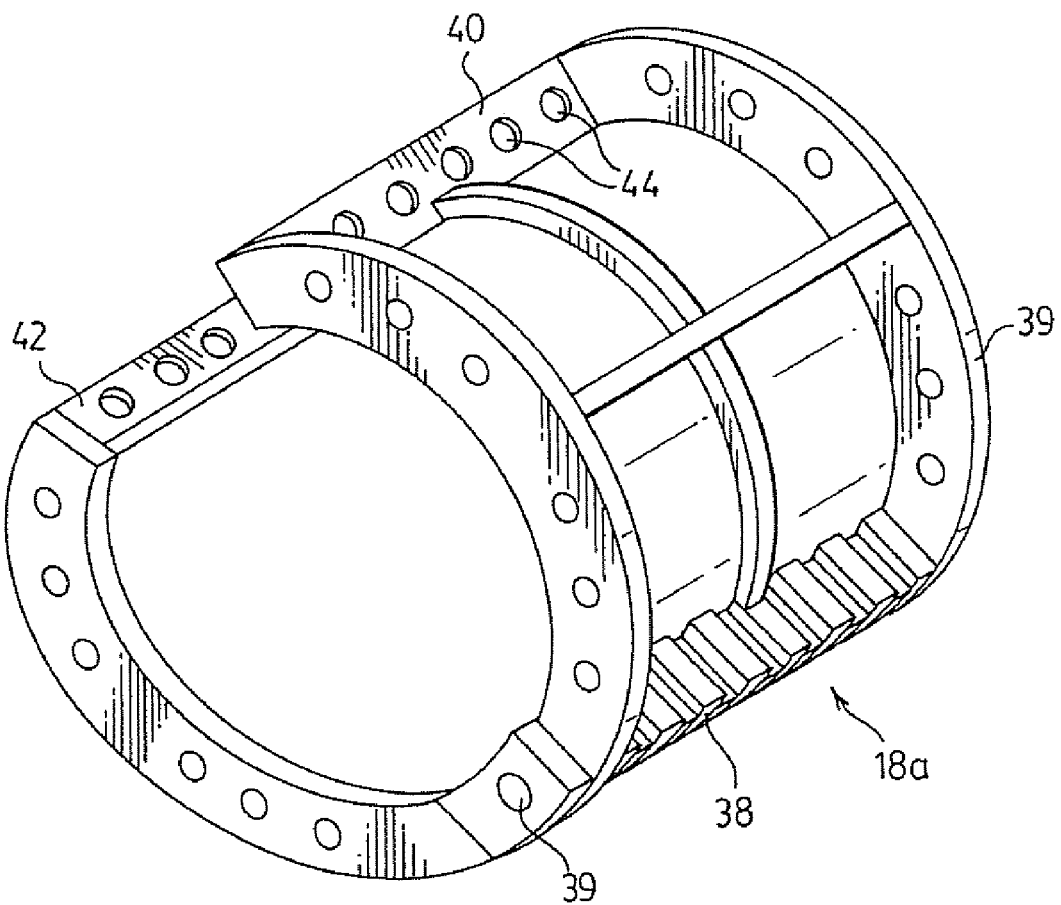

FIG. 3d illustrates a variation of the locking clamp of FIG. 3b. In this case, the locking clamp, shown as 46a for convenience, also includes a generally "C" shaped body with opposing flanges 47a and 48a. One of the flanges, for example 47a, is provided with a number of locating pins 49a adapted to be received into corresponding bolt holes 44 in flange 40 or 42 of the support clamp 18a as shown in FIG. 3e. In this embodiment, instead of hydraulic cylinders 50, the locking clamp 46a includes a number of integral hydraulic rams 51 provided on one of the flanges, for example 48a, of the locking clamp 46a. The rams 51 are positioned so as to extend, when actuated, in the direction of the opposite flange 47a of the locking clamp 46a. In use, the locking clamp 46a of FIG. 3d functions in the same manner as clamp 46 described above in reference to FIGS. 3a to 3b. It will be appreciated that the support clamp 18a is dimensioned in view of the diameter of the pipe so that, once placed on the pipe, the flanges 40 and 42 of the support clamp 18a are not in contact. Such an arrangement ensures that when the flanges 40 and 42 are forced together, the support clamp 18a is tightened around the circumference of the pipe thereby resulting in a tight frictional fit. The forcing together of the flanges 40 and 42 is accomplished by the locking clamp. Specifically, once the support clamp 18a is positioned on the pipe being tested, the locking clamp 46a is placed over both flanges 40 and 42 so that the locating pins 49a of the locking clamp 46a engage the corresponding bolt holes 44 of the flange 40 (it will be understood that the locating pins can alternatively engage the bolt holes of flange 42). In such an arrangement, the hydraulic rams 51 will be positioned against the flange 42. The hydraulic rams 51 are then actuated, thereby forcing flange 42 towards flange 40 and, in the result, forcing the support clamp 18a to tighten around the circumference of the pipe being tested.

In the above description, the support clamp 18 or 18a has been described as being connectable by bolts or hydraulic clamps. However, various other means of connecting the clamp will be apparent to persons skilled in the art and the present invention is not limited by such variations. For example, the support clamp 18 can be closed (i.e. connected) by means of a magnetic locking mechanism.

Figure 4:
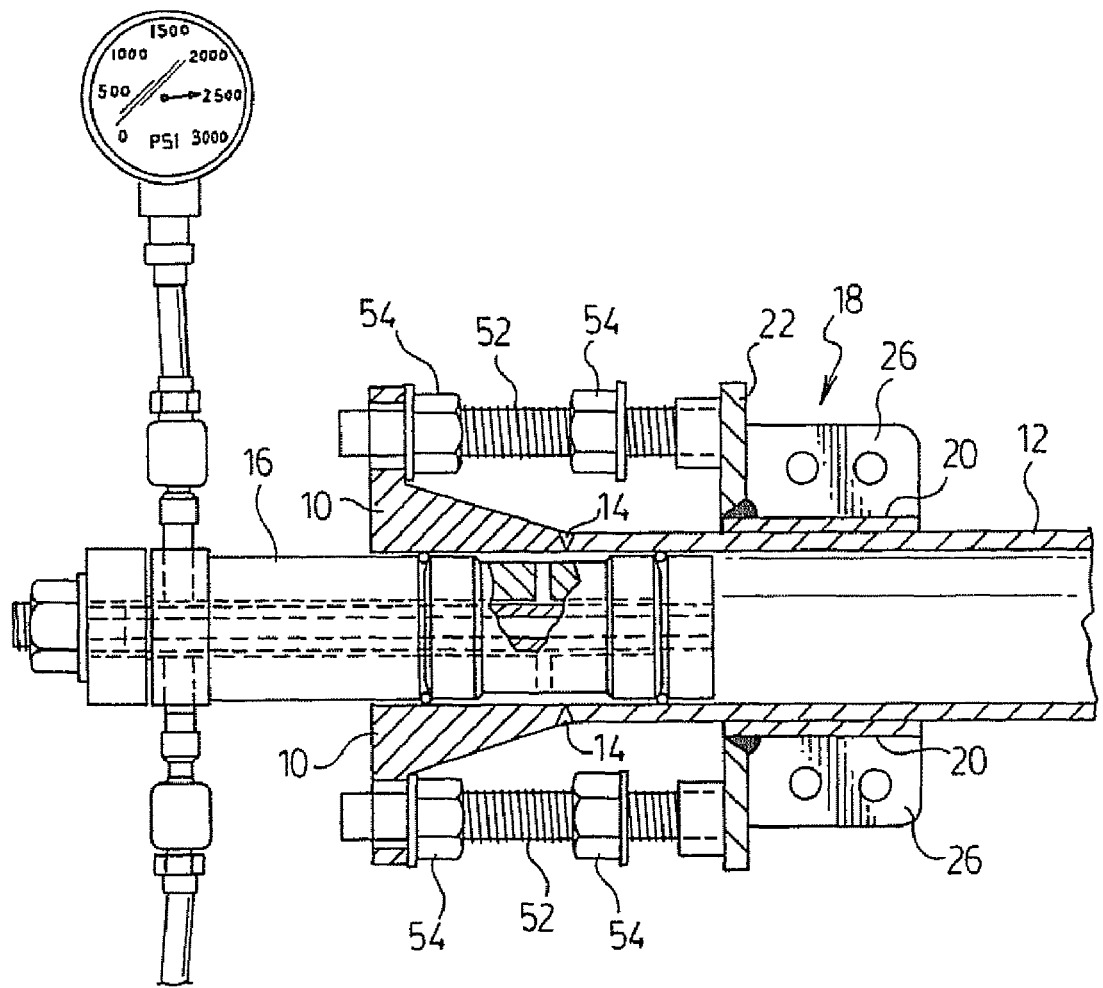
FIG. 4 is a cross sectional view of another embodiment of the invention.

FIG. 4 illustrates another embodiment of the invention shown in FIG. 1 wherein the hydraulic cylinders 28 of FIG. 1 are replaced with jack bolts 52. As illustrated, the jack bolts 52 perform the same function as the hydraulic cylinders 38 of FIG. 1. The jack bolts are provided with nuts 54 that can be tightened to exert the desired axial force against the flange 10. In a similar manner, it will be appreciated that the hydraulic cylinders or jack bolts etc. can be replaced with any other force applying device or mechanism.

Figure 5:
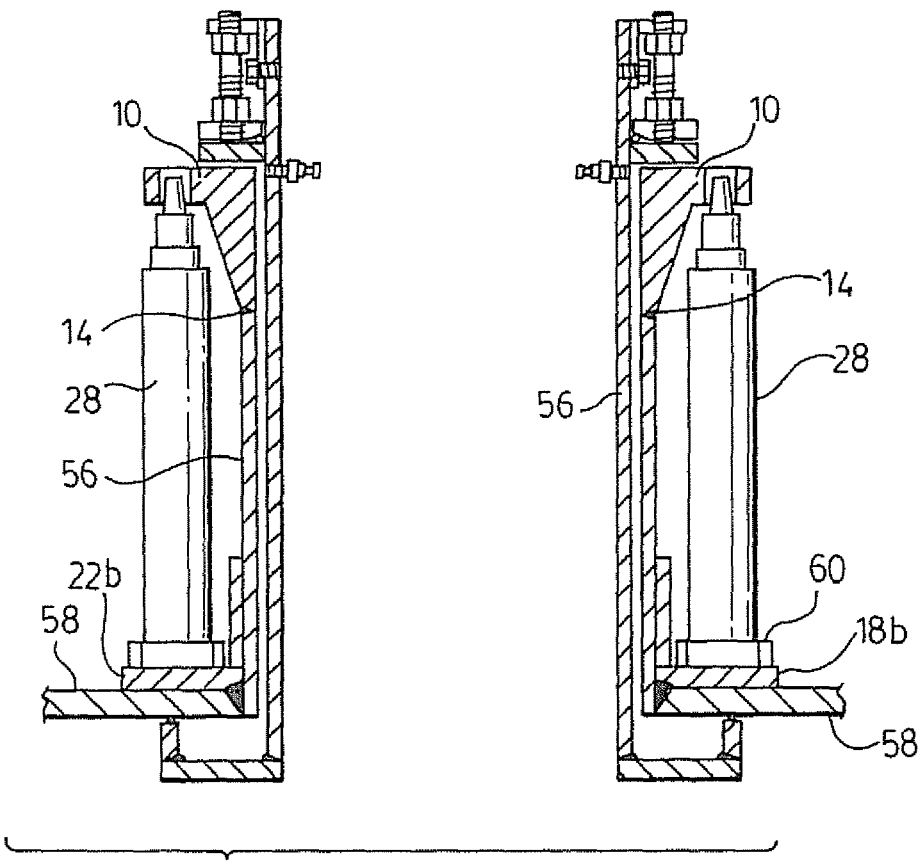
FIG. 5 is a cross sectional view of another embodiment of the invention.

FIG. 5 illustrates another embodiment of the apparatus of the invention wherein the flange 10 is provided on a vessel 11. In this embodiment, the flange 10 is connected to a pipe 56 extending from the wall 58 of a vessel. The flange 10 is connected to the pipe 56 by a weld 14. As in the embodiment of FIG. 1, the apparatus includes a support clamp 18b and hydraulic cylinders 28 for applying an axial force against the flange 10. As will be noted, the support clamp 18b of this embodiment is provided in an abutting arrangement with the vessel wall 58. Although the embodiment of FIG. 5 is illustrated with hydraulic cylinders 28 being used to apply the required axial force, it will be understood that other force applying mechanisms can be equally used. One such mechanism, as described above, may comprise jack bolts or other such devices.

Figure 6:
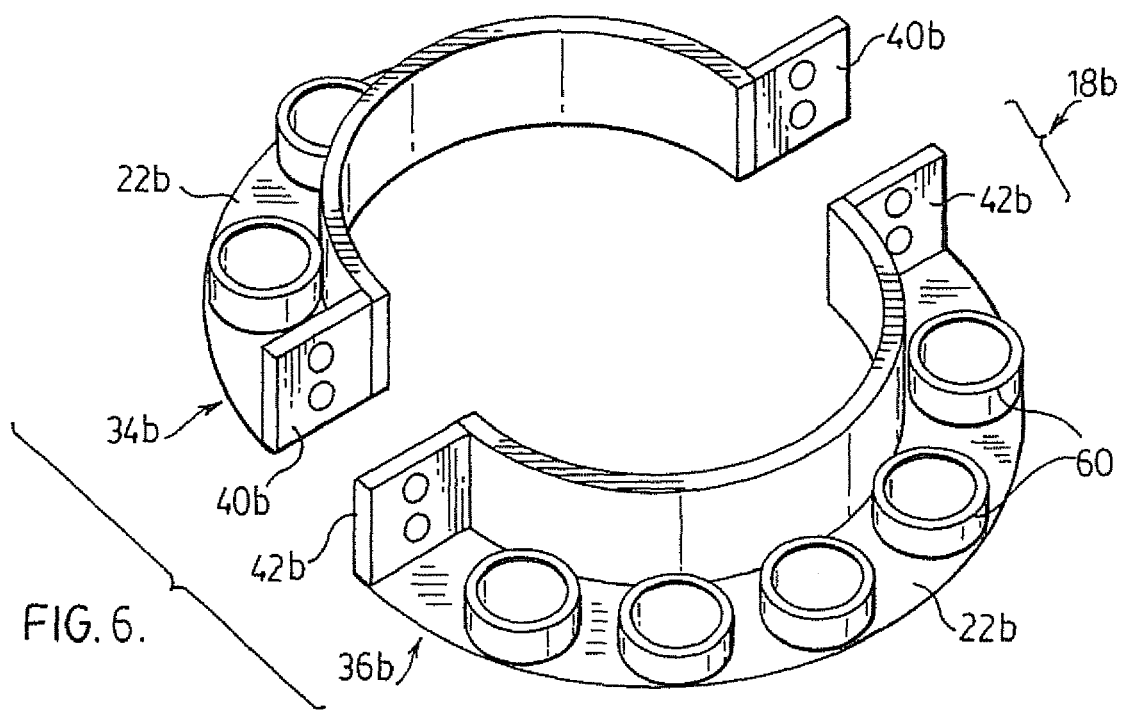
FIG. 6 is a perspective view of the support clamp of FIG. 5.

FIG. 6 illustrates the two sections 34b and 36b of the support clamp 18b shown in FIG. 5. The two sections 34b and 36b each include opposing flanges 40b and 42b, which have a similar function to the connecting ribs 40 and 42 described above in connection with FIG. 2. Once the sections 34b and 36b are positioned on the flange being tested, the flanges, or ribs, 40b and 42b can be connected together by means of bolts, hydraulic clamps (such as clamps 46 described in reference to FIG. 3b). As can be seen, the support clamp 18b preferably includes locating pockets or rings 60 circumferentially spaced thereon. The locating rings 60 are dimensioned to receive one end of the hydraulic cylinders 28 and position same along the area of the support clamp 18b. As will be appreciated, the locating rings 60 serve to positively locate the cylinders 28 on the support clamp 18b thereby facilitating the set up of the apparatus. It will be appreciated that locating rings such as those shown in FIG. 6 can also be provided on all support clamps described herein to obtain the same benefit. In a preferred embodiment, the locating rings 60 receive the base end of the hydraulic cylinder. In a further embodiment, the opposite, or actuating (i.e. moving) end, of the cylinder 28 is also received within a similar locating ring. In another embodiment, the locating rings 60 can be replaced with recesses provided on the respective bearing surface.

Figure 7:
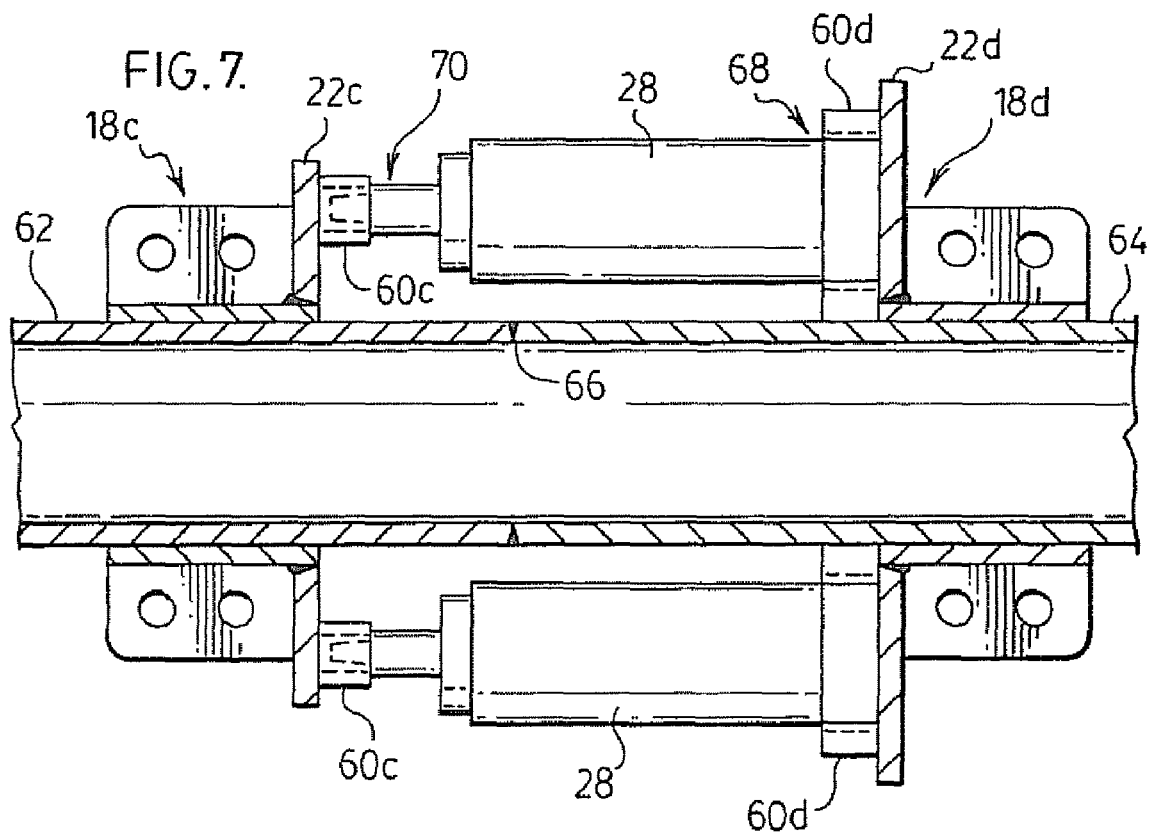
FIG. 7 is a cross sectional view of another embodiment of the invention as used on pipes.

FIG. 7 illustrates an embodiment of the invention wherein the weld to be tested serves to join two sections of pipe together. As shown, a pipe is comprised of sections 62 and 64, which are connected end to end in abutting arrangement by means of a weld 66. In order to apply the aforementioned axial stress on the weld 66, the apparatus of the invention includes two support clamps 18c and 18d provided on each of the pipe sections 62 and 64, respectively, whereby the weld 66 is located between both clamps 18c and 18d. The support clamps 18c and 18d are essentially identical in structure to the support clamp (18) shown in FIG. 1 and are secured to each pipe section as described above. Hydraulic cylinders 28 are positioned circumferentially around the pipe, extending between the support clamps 18c and 18d in a direction generally parallel to the longitudinal axis of the pipe. As shown in FIG. 7, the hydraulic cylinders 28 bear against the bearing rings 22c and 22d provided on support clamps 18c and 18d, respectively. In this arrangement, one of the bearing rings, for example 22d, is adapted to receive the base ends 68 of the cylinders 28 while the other of the bearing rings, for example 22c, is adapted to receive the actuating (i.e. moving) end 70 of the cylinders. Preferably the bearing rings 22c and 22d include locating pockets (i.e. recesses) or rings 60c and 60d, respectively, to receive the respective ends of the cylinders 28.

In the above description, reference has been made to hydraulic cylinders 28. However, as known to persons skilled in the art, the term hydraulic ram may also be used.

Figure 8:
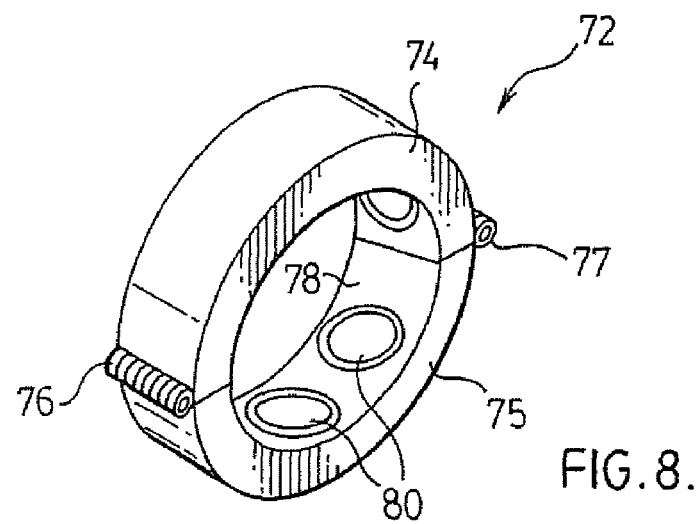
FIG. 8 is a perspective view of another embodiment of the support clamp of the invention.

FIG. 8 illustrates another embodiment of the support clamp of the invention. In this instance, the clamp shown generally at 72 comprises a ring formed from two sections 74 and 75. Each section is provided with cooperating halves of a hinge or similar closure such as shown at 76 and 77. In one embodiment, the hinge can be a plurality of overlapping rings, through which bolts can be extended. In another embodiment, one of the hinges can be permanently attached to the sections 74 and 75 enabling the sections to pivot thereon. In either case, the sections are designed to be placed around a pipe to be tested and connected together once placed. The sections 74 and 75 are also provided on the inner surface 78 with a plurality of circumferentially spaced hydraulic rams 80. The rams 80 may comprise for example low or ultralow profile rams as known in the art. An example of such rams are those manufactured by Enerpac; however, various other similar hydraulic rams will be apparent to persons skilled in the art. The rams 80 are positioned so as to direct the actuating ends or heads of thereof towards the center of the clamp 72. As will be understood, such an arrangement will cause the actuating heads of the rams 80 to extend radially inward. As will be explained further below, such an arrangement causes the rams 80 to apply pressure against the outer wall of the pipe to which the support clamp is applied.

Figure 9:
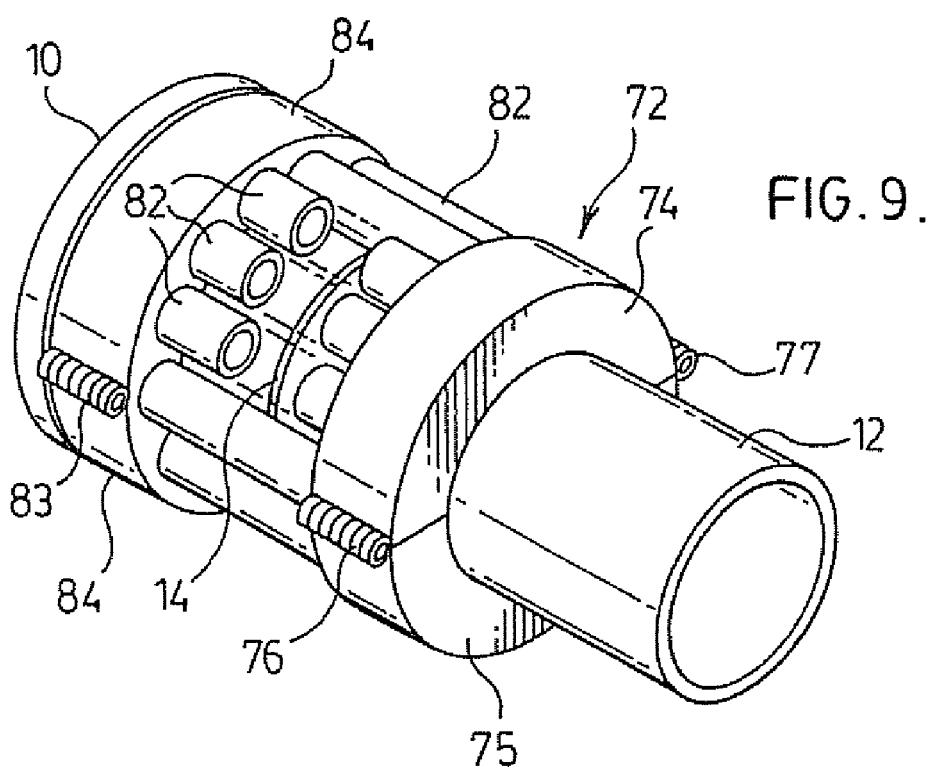
FIGS. 9 and 10 are perspective views of the clamp of FIG. 8 when in use.

FIG. 9 illustrates an application of the support clamp 72 of FIG. 8 when used on a pipe as in FIG. 1. As shown, the support clamp 72 is placed around the outer surface of the pipe 12 having attached thereto a flange 10 by means of a weld 14. The clamp 72 is positioned axially away from the flange 10. A number of hydraulic cylinders or rams 82 are provided on the support clamp 72 so as to be circumferentially spaced about the outer surface of the pipe 12 and extending generally parallel therewith. Some of the hydraulic rams 82 are shown cut away so as to illustrate the weld 14. The hydraulic rams, or cylinders 82 function in a manner similar to that described above. That is, one end, such as the base, of each ram 82 is placed against the support clamp 72. The opposite, actuating (or moving) end of each ram may be placed against the flange 10. However, as shown in FIG. 9, a spacer ring 84 may optionally be positioned around the flange wherein one side of the spacer ring 84 abuts the flange 10 while the other side is adapted to receive the actuating ends of the rams 82. As shown, the spacer ring 84 may comprise two sections connected by a hinge 83 and locked together once in position on the pipe or flange being tested.

Once the assembly is set up, as shown in FIG. 9, the low profile hydraulic rams 80 of the support clamp 72 are actuated whereby the actuating heads thereof apply a radially inward force against the pipe 12. It will be appreciated that the rams 80 are generally actuated simultaneously so as to apply an even pressure around the circumference of the pipe 12. The actuation of the rams 80 is continued until the desired force (described further below) is applied to the pipe 12. After this, the hydraulic cylinders or rams 82 are then actuated thereby resulting in an axial or longitudinal force being applied on the weld 14. It will be understood that the force applied by the cylinders 82 can be easily calculated and that, based on such calculation, the required counter-force, applied by the low profile rams 80 can then be calculated. The latter calculation will take into consideration the friction coefficient of the pipe 12 material.

Figure 10:
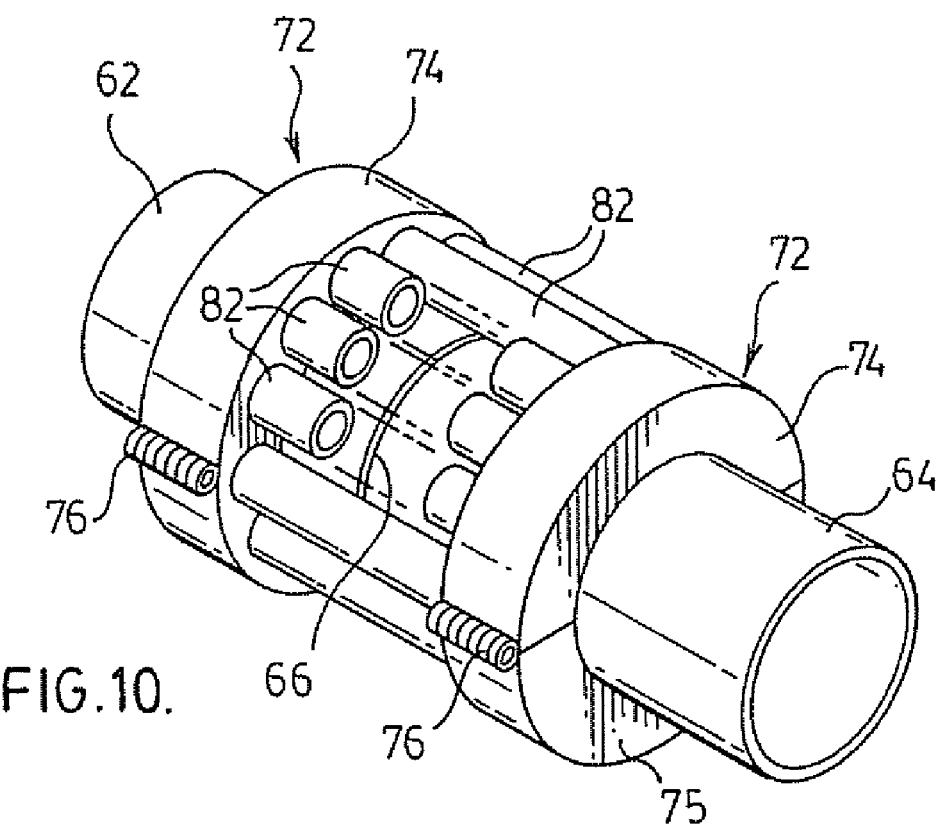

FIG. 10 illustrates the use of the support clamp 72 of FIG. 8 in the system of FIG. 7, wherein a weld 66 is used to connect two sections 62 and 64 of pipe. In this aspect, two support clamps 72 are used on opposite sides of the weld 66. The support clamps 72 are connected and secured to the respective section of pipe in the manner described above in reference to FIG. 9. A number of hydraulic cylinders or rams 82, similar to those described in reference to FIG. 9, are also provided. The cylinders 82 extend between both support clamps 72, whereupon, once the cylinders 82 are actuated, an axial separation force is applied against the weld.

Figure 11:
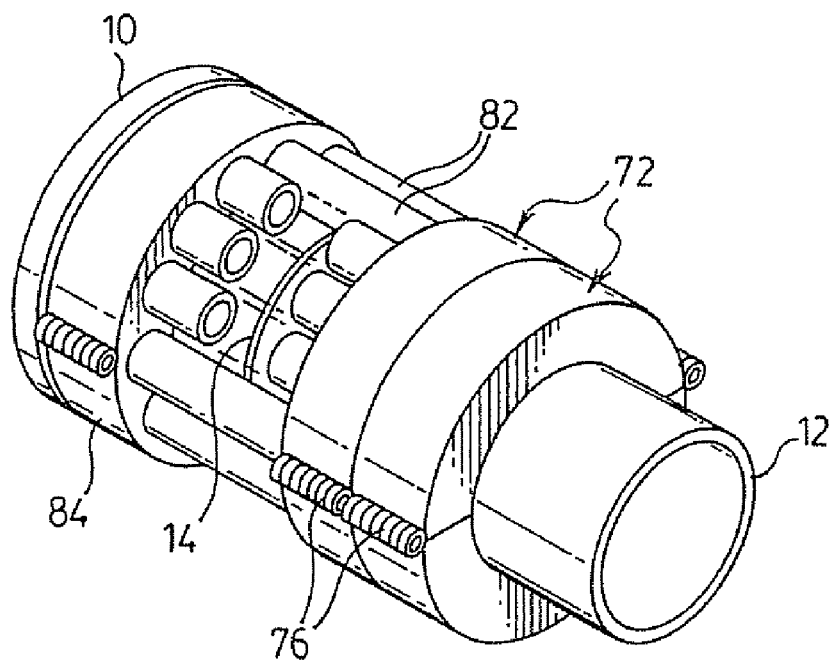
FIGS. 11 and 12 are perspective views of a modification of the embodiment illustrated in FIGS. 9 and 10.
Figure 12:
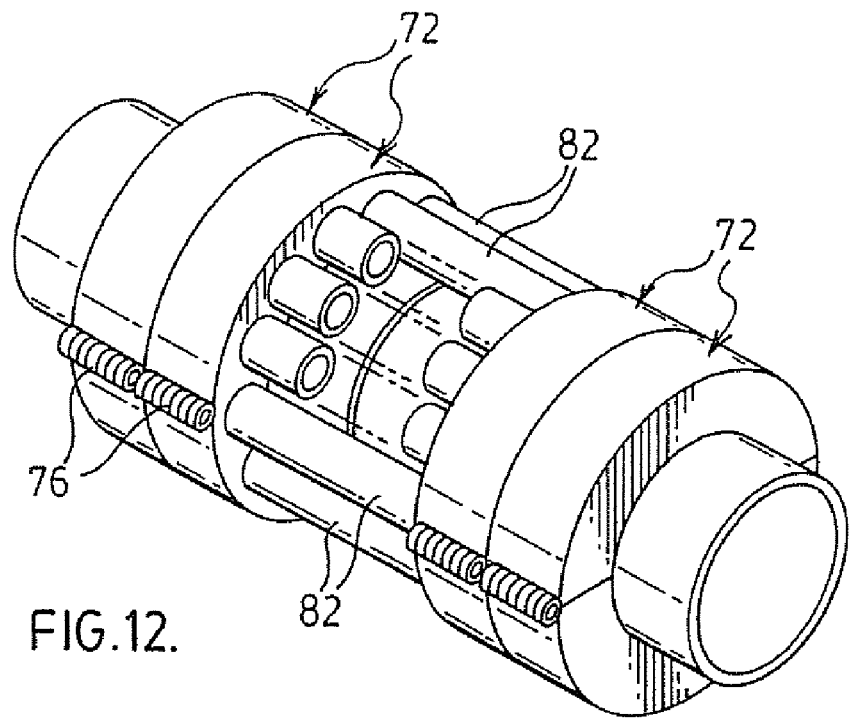

It will be appreciated that in the embodiments described above, more than one support clamp can be used in situations where extra clamping force is required. This is illustrated in FIGS. 11 and 12, which depict the apparatus of FIGS. 9 and 10, respectively, but where additional support clamps 72 are used. In another aspect, the support clamps can be provided with flanges or other similar means to enable adjacent support clamps to be joined together.

Figure 13:
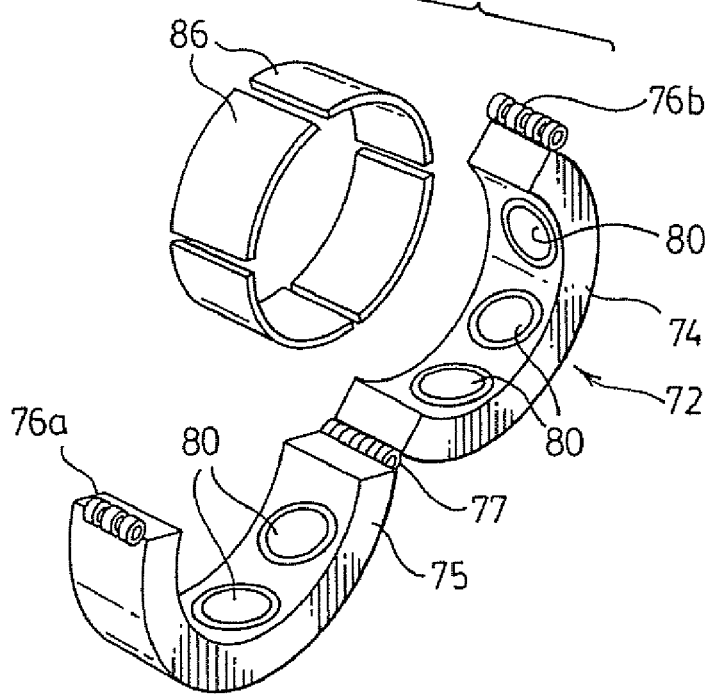
FIG. 13 is a perspective view of another embodiment of the support clamp of FIG. 8 shown in an open orientation.

In the clamp 72 of FIG. 8, it may sometimes be required to use load distribution pads such as those shown in FIG. 13. As shown, the support clamp 72 can be provided with a two or more load distribution pads 86 positioned between the low profile hydraulic rams 80 and the pipe to which the clamp 72 is to be attached. The pads 86 serve to transmit the force of the rams 80 to the pipe being tested. It will be understood that the pads 86 may be needed in cases where the wall thickness of the pipe is small, thereby avoiding damage to the pipe. In other cases, the pads 86 can be used to increase the frictional force applied by the clamp 72 against the pipe. The distribution pads 86 can be attached to the actuating heads of the low profile rams 80 or may be placed on the pipe to be tested prior to positioning the clamp 72. In another aspect, the distribution pads 86 can be joined together with hinges or links (not shown) so as to facilitate their placement around the pipe.

Figure 14:
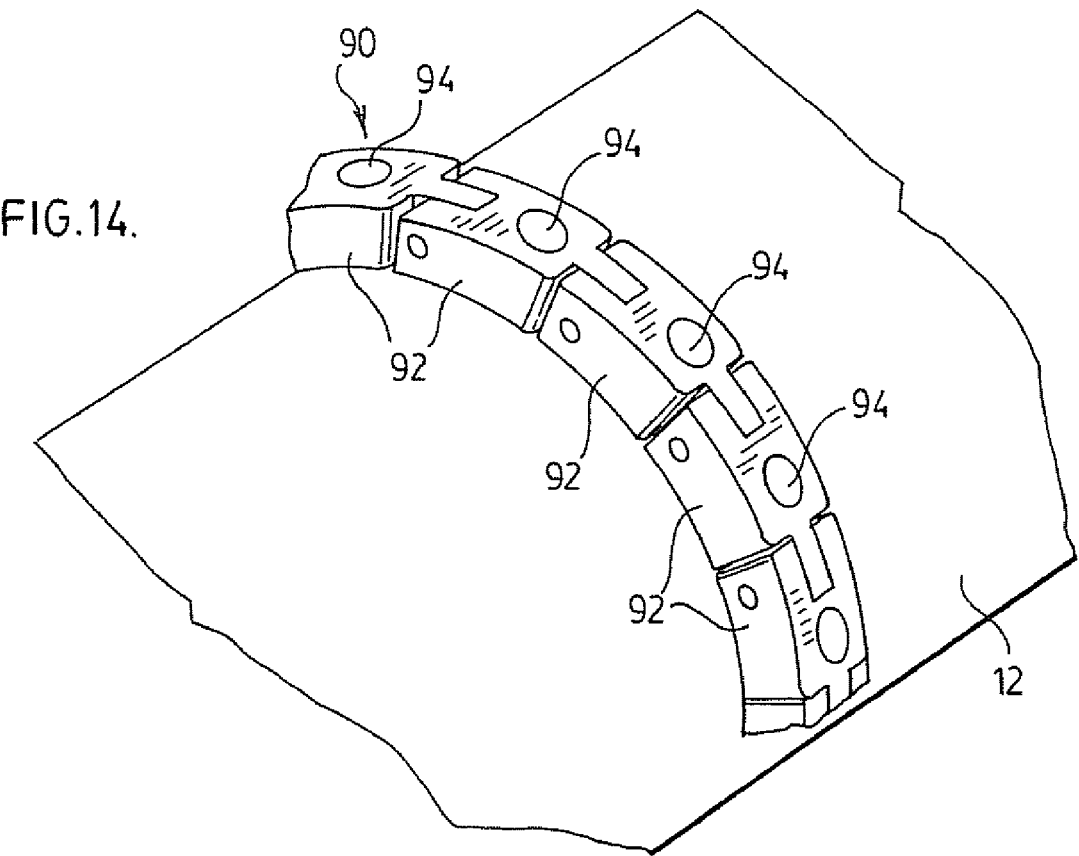
FIG. 14 is a perspective view of another embodiment of a support clamp.

FIG. 14 illustrates another embodiment of the support clamp of the invention. In this embodiment, the support clamp 90 is comprised of a plurality of links 92 each connected together in a chain-like formation. Each link 92 includes a magnet 94, and preferably an electromagnet, that is capable of being connected to the pipe 12 being tested. In use, the required number of links 92 are connected together so as to accommodate the circumference of the pipe 12. Once in position, the magnets 94 are activated thereby causing an attractive force to be formed between the magnets and the pipe 12. It will be understood that the embodiment of FIG. 14 can be used with steel pipes 12. In one embodiment, the links 92 are made of a non-magnetic material such as aluminum or stainless steel.

Figure 15:
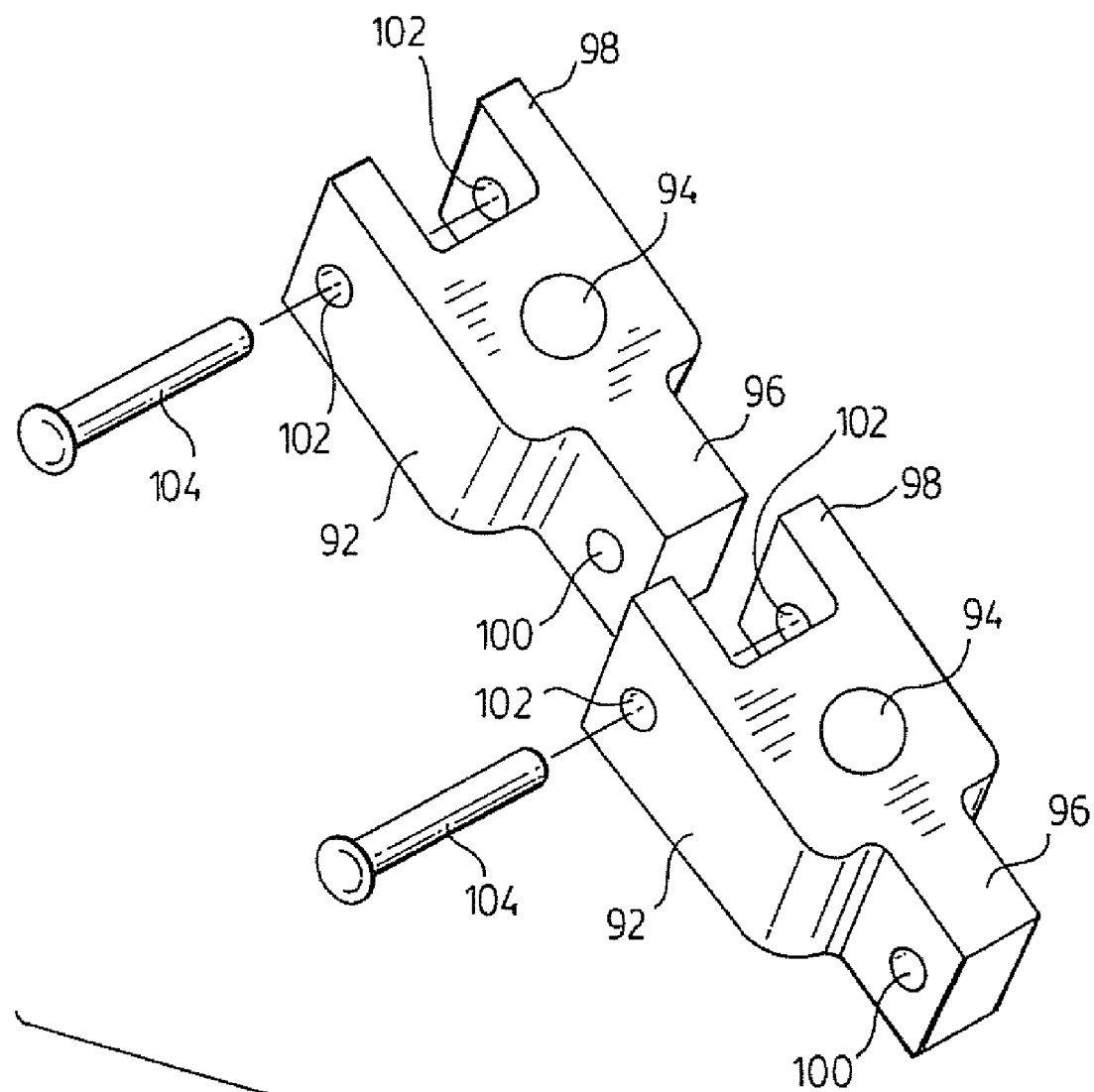
FIG. 15 is an exploded perspective view of the links forming the clamp of FIG. 14.

FIG. 15 illustrates the connection system used for joining the links 92 of the clamp 90 of FIG. 14. As shown, each link 92 is provided with interconnecting male 96 and female 98 ends. Each of the male and female ends 96 and 98 are provided with a bore 100 and 102, respectively, extending therethrough. The bores 100 and 102 are designed to be in alignment when the male and female ends of adjacent links 92 are brought together. Once the bores 100 and 102 are in alignment, a locking pin 104 can be inserted therethrough, thereby securing the links 92 together.

FIG. 15 also illustrates the electromagnets 94 provided on each link 92. It will be appreciated that the magnets 94 can be embedded within the links 92 and not exposed. Each link includes an electrical connection (not shown) to a power source, which serves to activate the magnets 94.

Figure 16:
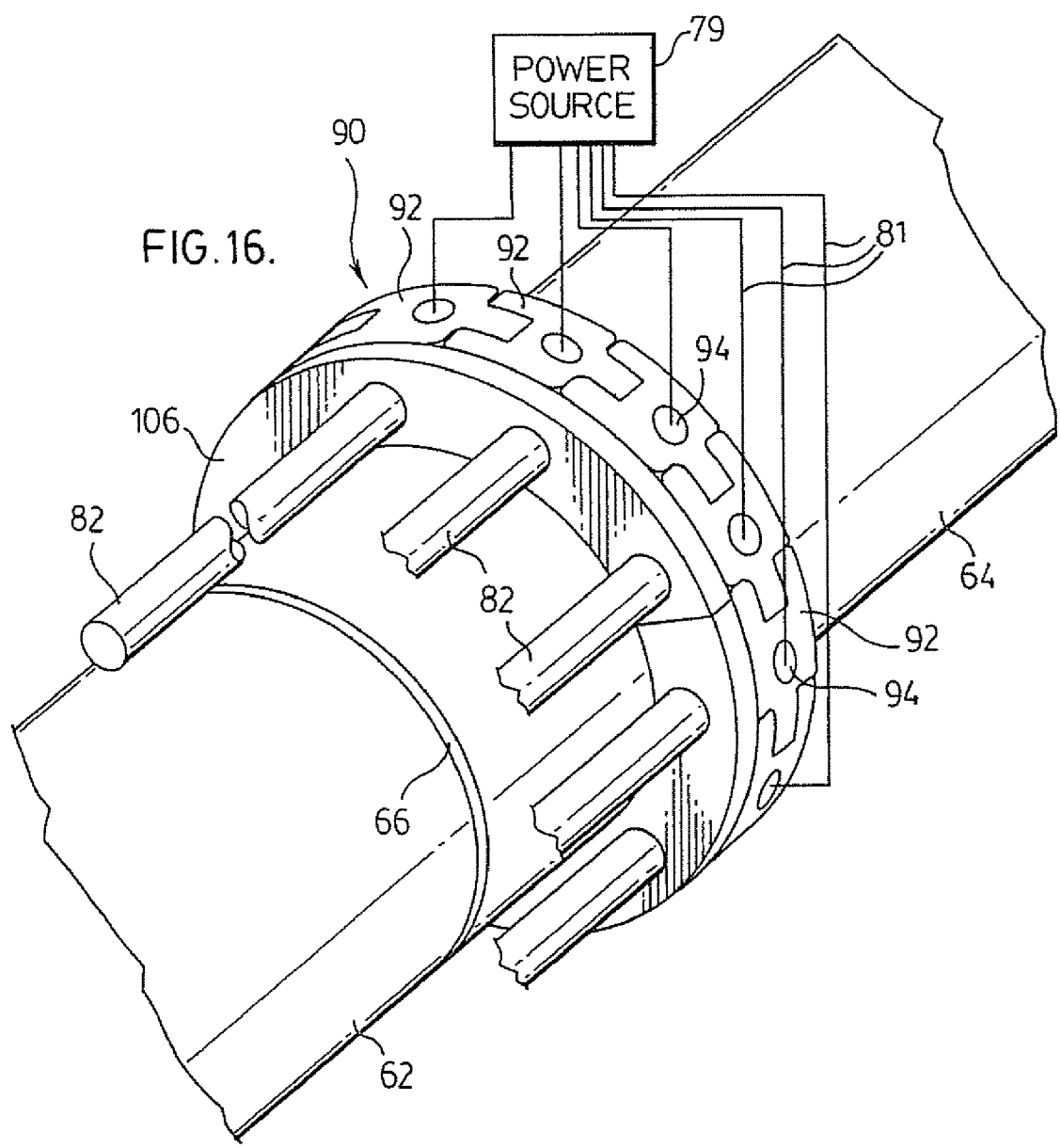
FIG. 16 is a perspective view of the clamp of FIG. 14 in use.

FIG. 16 illustrates the use of the clamp 90 of FIG. 14 when used in the manner shown in FIG. 11. As shown, the clamp 90 is provided on one section 64 of a pipe connected to another section 62 by a weld 66. Between the clamp 90 and the weld 66 is positioned a support plate 106 against which the bases of hydraulic cylinders or rams 82 are positioned. The actuating ends (not shown) of the cylinders 82 abut against a reaction plate (not shown), which is similar to the support plate 106. On the opposite side of the reaction plate is provided a further clamp such as that shown at 90. The cylinders 82 are then used in the same manner described above. FIG. 16 also schematically illustrates a power source 79 for supplying power to the magnets 94. The magnets 94 may be individually connected to the power source 79 by means of electrical leads 81.

Figure 17:
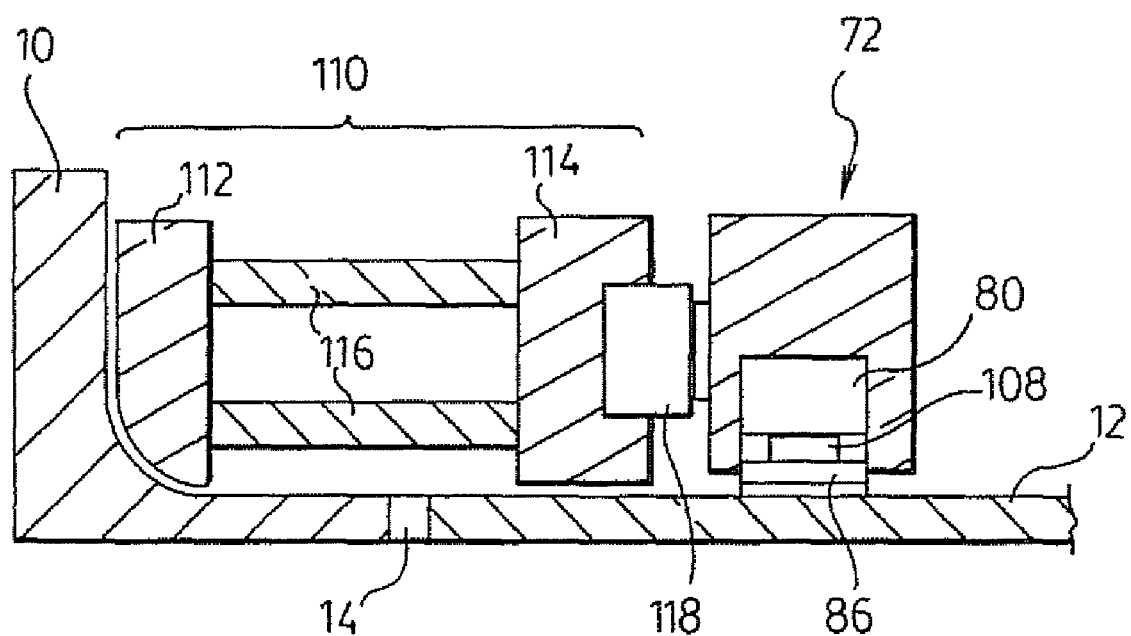
FIG. 17 is a partial cross sectional view of another embodiment of the apparatus of the invention.

FIG. 17 illustrates a further embodiment of the invention wherein the clamp of FIG. 13 is used. As shown, the clamp 72 is provided on a pipe 12 having a flange 10 joined by a weld 14. The clamp 72 is mounted around the circumference of the pipe 12 as described above. The clamp 72 is provided with a number of low profile hydraulic rams 80 arranged generally equidistantly around the circumference of the pipe 12. The rams 80 include actuating heads 108 that extend towards the outer wall of the pipe 12. As described above, the clamp 72 is provided with two or more load distribution pads 86 for transmitting the force applied by the rams 80 to the pipe 12. As also illustrated in FIG. 17, on the opposite side of the weld 14 (that is, opposite to the clamp 72), there is provided an alternative to the spacer 84 described above. In this case, the spacer 110 includes two annular blocks 112 and 114 provided around the circumference of the pipe 12 and straddling (i.e. on opposite sides of the weld 14. The blocks 112 and 114 will normally be provided in sections, such as two halves, so as to permit placement around a pipe. As discussed above, such sections can be connected by hinges or any other means and will include a means of locking them together once placed around the pipe being tested. The spacer also includes a number of connecting rods 116 joining the blocks 112 and 114. As shown, the connecting rods 116 overlap the weld 14. One of the blocks 112 is provided abutting the flange 10 while the opposite block 114 is provided abutting the support clamp 72. One of the blocks, such as block 114 as shown in FIG. 17, is provided with a number of hydraulic rams 118, such as the low profile rams discussed above. The rams 118 are arranged circumferentially around the pipe 12 and are positioned to extend, when actuated, in a direction generally parallel to the axis of the pipe 12, when the apparatus is in position. As shown in FIG. 17, the placement of the hydraulic rams 118 serves to apply an axial force against the support clamp 72 when actuated. Since the clamp 72 is prevented from moving axially on the pipe 12, such force is then transmitted, via the connecting rods 116 to the opposite block 112 and, subsequently, to the flange 10. As will be understood, the rams 118 can, alternatively or additionally, be provided on block 112. The connecting rods 116 may be extendable so that they can be sized to various lengths as needed to facilitate set up of the apparatus. Further, the number and positioning of the rods 116 between the blocks 112 and 114 will depend upon the diameter of the pipe being tested and on the axial forces applied. The hydraulic rams 118 provided on the blocks 112 and/or 114, may also include load distribution pads as well to transmit the forces generated by the rams 118. It will be understood that such pads, although not shown, will be designed for such purpose and may comprise, for example, two crescent shaped pads, which combine to form an annular disc.

It will be appreciated that the advantage of the apparatus shown in FIG. 17 lies in the fact that the weld 14 can be observed during the testing thereof using methods as described above. It will also be appreciated that although FIG. 17 depicts a weld joining a flange 10 to a pipe, the apparatus can equally be used in situations where two sections of pipe are joined together as in FIG. 10, 12, or 16, for example.

In the above description, it will be understood that in addition to any number of support clamps that can be used during the testing process, the types of clamps (such as the ones described above) may also be used in various combinations. That is, two or more of the different clamps described above can be used in combination when conducting a test.

The cylinders, rams or jacks used to apply the aforementioned axial force have been referred to in plural tense. However, it will be understood that in another aspect, it would be possible in certain cases for a single such apparatus to be used for achieving the desired axial force or stress. Similarly, although the above description has made reference to several examples of the axial force applying means, it will be understood that any other mechanism can be used for the desired result.

It will be understood that the above discussion has used geometric terms such as annular, disc, circumference, etc., for ease of reference. However, these terms should not be construed as limiting the invention to any specific shape of nozzle or pipe and various modifications of the apparatus will be apparent to persons skilled in the art to adapt same to any shape or design.

Although the invention has been described with reference to certain specific embodiments, various modifications thereof will be apparent to those skilled in the art without departing from the spirit and scope of the invention as outlined in the claims appended hereto. The disclosures of all prior art recited above are incorporated herein by reference in their entirety.

EXAMPLE

The present invention will now be illustrated by means of the following example. The example is not intended to limit the scope of the invention in any way.

In this example, an apparatus similar to that shown in FIG. 1 was used. The pipe testing assembly (i.e. pipe and flange) was fabricated from 8.625 inch×0.322 inch (21 cm×0.82 cm) Schedule 40 pipe with a 150# Class weld neck flange. Four support clamps were secured to the pipe portion of the test assembly to form a "clamp assembly". Following this, four circumferentially spaced hydraulic cylinders were connected to the clamp assembly and mounted against the flange as shown in FIG. 1. Each of the cylinders had a pressure area of 1 in$^2$ (6.45 cm$^2$). A hydraulic pressure system was then connected to the cylinders. A displacement transducer was used to record any potential displacement of the clamp assembly during testing. No appreciable axial displacement occurred during the testing process, which verified that the clamp was rigidly attached to the pipe during testing.

Two types of tests were conducted in this evaluation. The first test involved the application of axial loading using the hydraulic cylinders with no internal pressure in the pipe assembly. Strain gauges installed on the outside surface of the testing assembly were used to monitor axial and hoop stresses. The second test involved the installation of the in situ hydrotest device (which corresponds to the testing tool 16 shown in FIG. 1) that applied internal pressure to the inside surface of the flange end of the testing assembly, while the hydraulic cylinder assembly was used to generate pressure end loading.

Test 1: Axial Loading With No Internal Pressure

This test served to assess the axial loading, resulting from the hydraulic cylinders. FIG. 18 illustrates the hoop and axial stresses developed during the test as functions of elapsed time and hydraulic ram pressure. Because each of the cylinders had a pressure area of 1 in$^2$, every "psi" of hydraulic pressure generates an axial load of 4 lbs. The purpose of this test was to evaluate the ability of the hydraulic loading unit to simulate a pressure end load. The results confirmed that without internal pressure in the testing assembly the hydraulic rams generate axial stresses as expected. Sample data from this test is provided below:

a) hydraulic cylinder pressure applied=5,409 psi (generating an axial force of 21,636 lbs)

b) Measured axial stress=2,660 psi c) Calculated axial stress=2,575 psi (based on pipe cross sectional area of 8.4 in$^2$)

As shown in the above data, the difference between the calculated and measured axial stress values differs by 3.2%.

Test 2: Axial Loading With Internal Pressure (Using in Situ Testing Tool)

Once testing to assess the ability of the hydraulic cylinders to generate axial stresses was complete, the second phase of testing was started. This effort involved using the in situ hydrotest tool (or testing tool) along with the axial loading assembly. The steps involved during this phase of testing basically involved the following steps:

1) The hydrotest tool was inserted into the pipe/flange test assembly, the latter having already been fitted with the axial test assembly (i.e. clamp assembly and hydraulic cylinder assembly) as described above in Test 1.

2) The tool was tightened to ensure a proper seal.

3) An internal pressure was applied to the testing assembly. The applied pressure was 450 psi to represent the hydrotest pressure for the 150# class assembly.

4) The hydraulic cylinders were then actuated to apply an axial load to represent the pressure end load.

Pressure and tension measurements were taken during the steps listed above. In the course of such measurements, it was found that the loading generated by the testing tool itself results in the generation of hoop stress, but no axial membrane stress. Once the hydraulic cylinders were actuated, loading was generated by both the internal pressure of the testing tool as well as the axial loads applied by the hydraulic cylinders. In the latter case, the measured axial and hoop stresses exceeded the calculated stresses. Once the hydraulic cylinders were engaged, they generated additional hoop stress that resulted in a final hoop stress of approximately 8,000 psi.

In this example, testing and analysis to assess the performance of the enhanced hydrotest system incorporating hydraulic cylinders to generate pressure end loading. Initial evaluation involved testing only the hydraulic cylinders by themselves and the results indicated that the correct axial stress level was achieved. Further testing revealed that when combined with the hydrostatic testing tool, axial and hoop stresses were generated that exceeded those that would be developed in a conventional hydrostatic test.

The conclusion based on a review of the analysis and testing results is that it is possible to generate the hoop and axial stresses associated with a conventional hydrostatic test using an in situ hydrostatic testing tool. Further, as noted above, the clamping assembly was found to provide sufficient clamping force to support the hydraulic cylinders.

I claim:

1. A method for testing the integrity of a weld on a pipe comprising:

subjecting a region of the pipe including said weld simultaneously to an axially expansive force and a radially expansive force, each of said forces being less than the strength tolerance of the weld or the pipe, said axially expansive force being applied in a direction generally parallel to a longitudinal axis of said pipe said radially expansive force being applied by a pressurizing fluid; and, monitoring the pressure of said pressurizing fluid.

2. The method of claim 1 wherein said method comprises:

providing at least two supports on the outer surface of the pipe, said supports being axially spaced along the pipe and positioned on opposite sides of the weld;

securing said supports to said pipe for preventing axial movement of said supports along said pipe;

providing at least one force applying device between said supports for applying an axial force against said supports; and, actuating said devices thereby subjecting said weld to an axial stress.

3. The method of claim 2 wherein said axial force is applied equally around the circumference of said pipe.

4. The method of claim 3 wherein at least one of said at least two supports comprises a flange connected to said pipe.

5. The method of claim 4 wherein said flange is connected to said pipe by said weld.

6. The method of claim 5 wherein at least one of said at least two supports comprises a clamp mounted on the outer surface of said pipe.

7. An assembly for use in testing the integrity of a weld on a pipe, the assembly comprising:

at least two supports provided on the pipe and extending circumferentially around said pipe, said supports being axially spaced along the pipe and positioned on opposite sides of the weld, said supports being secured to said pipe thereby preventing axial movement of said supports along said pipe;

at least one axial force applying device positioned between said supports, said device being adapted to apply an axially expansive force against said supports in a direction generally parallel with a longitudinal axis of said pipe a means for applying a radially expansive force within an internal region of the pipe including said weld, said radially expansive force being applied with a pressurized fluid; and, a means for monitoring the pressure of said pressurizing fluid while both of said forces are applied simultaneously and each of said forces are less than the strength tolerance of the weld or the pipe.

8. The assembly of claim 7 wherein said supports include at least one bearing surface against which said force applying devices bear.

9. The assembly of claim 7 wherein at least one of said at least two supports comprises a circumferential clamp mounted on the exterior of said pipe.

10. The assembly of claim 9 wherein said clamp is comprised of two or more sections.

11. The assembly of claim 7 wherein at least one of said at least two supports comprises a flange connected to said pipe.

12. The assembly of claim 7 wherein said at least one force applying device is chosen from the group consisting of hydraulic cylinders, jack bolts and hydraulic rams.

13. The assembly of claim 7 wherein said force applying devices directly act on said supports.

14. The assembly of claim 7 wherein said assembly further includes a separator ring for transferring forces from said force applying devices to one or more of said supports.

15. The assembly of claim 9 wherein said circumferential clamp comprises:

a generally annular shaped collar having an outer diameter and an inner diameter and being adapted for placement around the circumference of said pipe;

a plurality of hydraulic rams provided within said collar, said rams having an actuating cylinder extendable radially in a direction towards the center of said collar;

wherein said rams are generally equidistantly spaced whereby, upon actuation of said rams, said cylinders apply a generally equal force against the outer surface of said pipe.

16. The assembly of claim 9 wherein said circumferential clamp comprises:

a plurality of links connected together to form a chain, said chain being sized to cover the circumference of said pipe;

each of said links including a connection means for connecting to adjacent links;

each of said links including an electromagnet, connected to a power supply, whereby upon activation of said power supply, said electromagnets engage the outer surface of said pipe.

* * * * *